United States Patent [19]

Mapes et al.

[11] Patent Number: 5,439,449
[45] Date of Patent: Aug. 8, 1995

[54] FLOW VISUALIZATION NEEDLE SYSTEM

[75] Inventors: Harold C. Mapes, Queensbury; William M. Appling, Hartford; Michael P. Cody; Eamonn P. Hobbs, both of Queensbury, all of N.Y.

[73] Assignee: E-Z-Em, Inc., Westbury, N.Y.

[21] Appl. No.: 231,276

[22] Filed: Apr. 22, 1994

[51] Int. Cl.[6] ............................................. A61M 5/00
[52] U.S. Cl. ................................... 604/164; 604/264
[58] Field of Search .......................... 604/264, 164-169, 604/272, 171, 173, 177, 118; 128/763, 765, 770, 771

[56] References Cited

U.S. PATENT DOCUMENTS

| | | | |
|---|---|---|---|
| 4,655,750 | 4/1987 | Vaillancourt | 604/165 |
| 5,092,845 | 3/1992 | Chang | 604/164 |
| 5,122,121 | 6/1992 | Sos et al. | 604/167 |
| 5,306,254 | 4/1994 | Nash et al. | 604/168 |

*Primary Examiner*—John D. Yasko
*Attorney, Agent, or Firm*—McAulay Fisher Nissen Goldberg & Kiel

[57] ABSTRACT

A needle system which upon arterial entry provides a visual indication of pulsatile blood flow. The needle system includes an elongated needle with distal and proximal ends. There is a needle hub at the proximal end of the needle and a port position between the proximal needle end and proximal hub end. The visualization connector tube having two ends is provided. The tube is sufficiently clear to permit visualization of material held therein. The first end of the tube is in communication with the port. An elastomeric reservoir is provided. The reservoir is in free, direct, unrestricted two-way communication with a second tube end. The needle, needle hub, and tube all have predetermined volumes. The reservoir has an initial unexpanded state with a first pressure and a first volume and a second state expanded with a second pressure and a second volume. Air pressure in the needle system is increased upon arterial entry. The increase in air pressure compresses and displaces the air in the needle system allowing blood to migrate into a portion of the connector. This air compression and displacement results in a decrease of the volume of air in the system while the volume in the reservoir increases.

13 Claims, 1 Drawing Sheet

FLOW VISUALIZATION NEEDLE SYSTEM

BACKGROUND OF THE INVENTION

The following invention relates to a needle system, and more particularly to a needle system which can be used during angiographic procedures.

At the beginning of an angiographic procedure, a needle is placed into an artery, such as the femoral artery. It is important to confirm that the needle is in an artery and one method of doing this is to visualize the blood exiting from the needle, which will have pulsatile flow if the needle is in an artery. Upon entry, the physician is forced to quickly insert the guidewire in order to stop the pulsatile flow of blood from the artery. Consequently, there is very limited time to adjust needle position to ensure optimal needle placement and location. Due to the pulsatile nature of the arterial flow, health professionals may inadvertently come in contact with the blood. To prevent the spread of blood-borne infections it is important to limit or prevent such contact.

Needle assemblies, which permit visualization of the arterial blood and which protect health professionals from inadvertent contact with the arterial blood are known in the art. One example of such a needle assembly is U.S. Pat. No. 5,122,121 entitled "Safety Needle Assembly". Although the needle assembly of '121 patent is a useful assembly, the visualization of arterial pulsatile blood pressure can be cumbersome.

Further, the needle assembly of the '121 patent includes a relatively large, collection bag which when filled with blood becomes cumbersome. Further, the needle assembly of '121 incorporates a 3-way stopcock which if inadvertently left in the open position will allow pulsatile arterial blood flow to exit the needle assembly. Another needle which provides for visualization of blood flow is the Arrow-Fischell Vascular Access Needle which has an abnormally long, rigid and thus cumbersome hub portion in which the arterial pulse can be observed.

It is an object of the present invention to provide a needle system which permits easy visualization of the flow of arterial blood therein.

It is another object of the present invention to provide such a system which is as similar to conventional arterial access needles as possible while being relatively small and easy to use.

It is a further object of the present invention to provide such a needle system which protects the health professional from inadvertent contact with the arterial blood.

It is another object of the invention to provide a means of needle system access that affords the physician unlimited time to safely place the needle and guidewire into the artery without blood loss.

It is another object of the invention to provide visual pulsatile optimization that allows subtle needle manipulation or fine tuning to ensure optimal needle placement within the artery.

It is a further object of the present invention to provide a means for test injection of imaging agents concurrently with the placement of the needle or needle and guidewire for the purposes of verifying needle and or guidewire placement and location while maintaining pulsatile blood flow visualization.

BRIEF DESCRIPTION

The present invention relates to a vascular access needle system. The needle system includes an elongated needle with a distal end and a proximal end. The system further includes a needle hub at the proximal end of the needle and a port positioned between the proximal end of the needle hub and the proximal needle end. A visualization connector tube is provided having first and second ends. The tube is sufficiently clear to permit visualization of material held therein. The first end of the tube is in communication with the port. The system includes an elastomeric reservoir. The elastomeric reservoir is in free, direct, unrestricted two-way communication with said second tube end. The reservoir is housed in a rigid enclosure and is connected to a syringe activated valve or stopcock which allows test injection of imaging media for flouroscopic arterial visualization. The rigid enclosure protects the reservoir from over expansion or compression during manipulation and use. The needle, the needle hub, and the tube all have predetermined volumes. The reservoir has a first state with a first pressure and a first volume and, a second state with a second pressure and a second volume. The second pressure is determined by the vascular blood pressure. The second reservoir volume and pressure are greater than the first reservoir volume and pressure. The volumes of the needle, hub, tube and reservoir are proportioned such that an average blood pressure will be visually represented within the middle section of the tube. This is accomplished by the elastomeric reservoir and compressability of air contained therein, which provides a spring mechanism to oppose the force of the blood pressure. In the preferred embodiment, this spring mechanism is a column of air contained within the tube and elastomeric reservoir.

DETAILED DESCRIPTION OF THE PREFERRED EMBODIMENT

Figure 1:
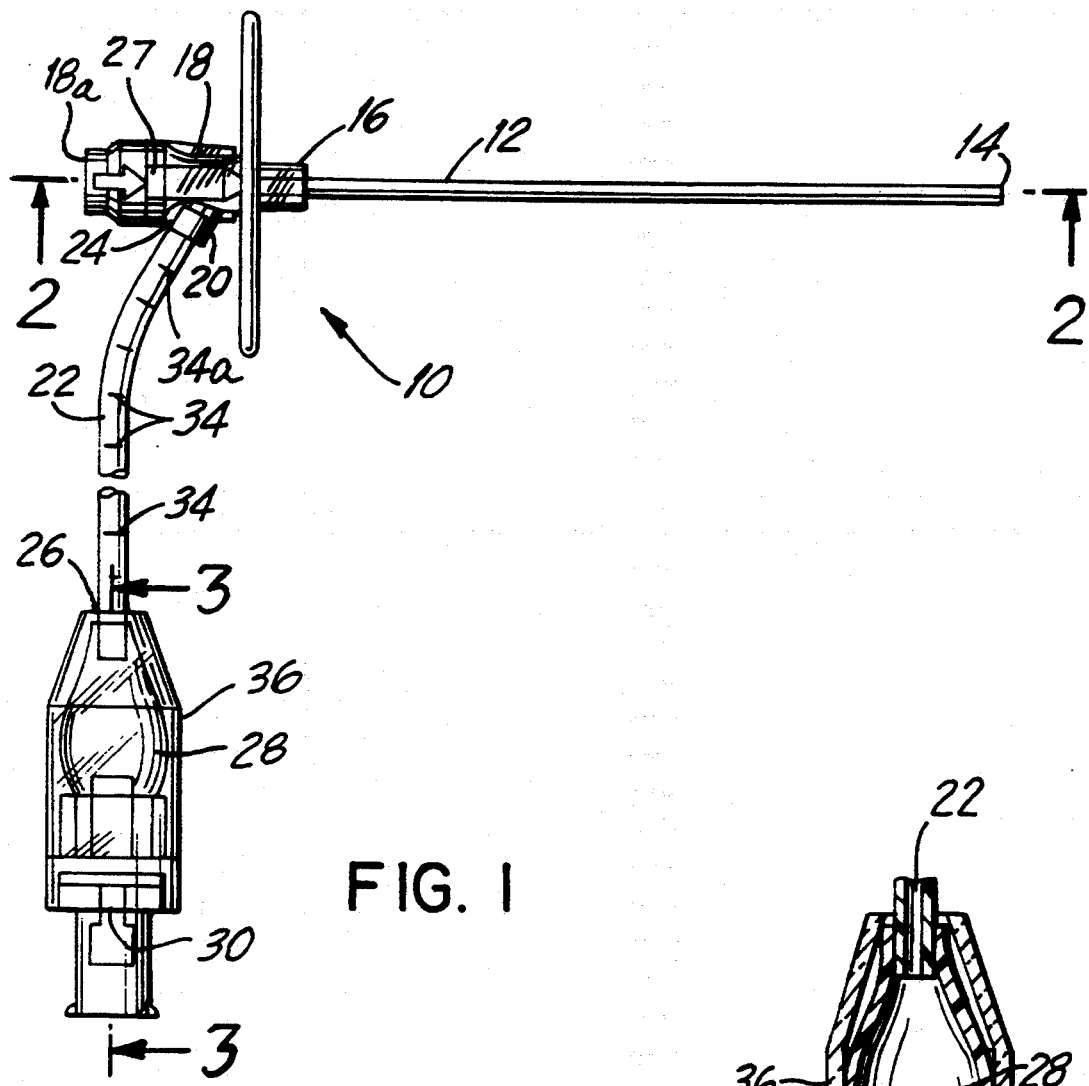
FIG. 1 is a perspective view of the needle system of the present invention.
Figure 2:
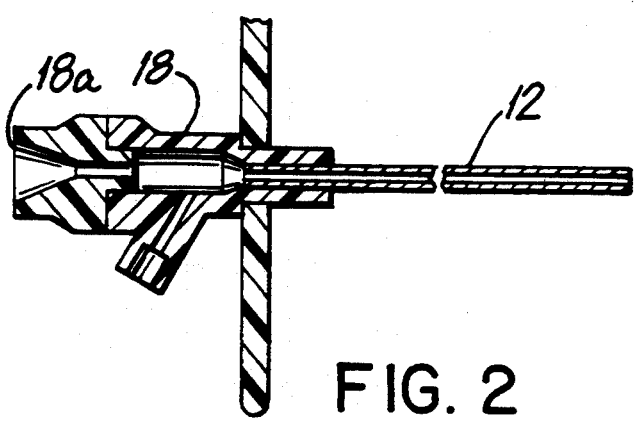
FIG. 2 is a sectional view of the hub portion of the FIG. 1 needle system taken along line 2—2 of FIG. 1.
Figure 3:
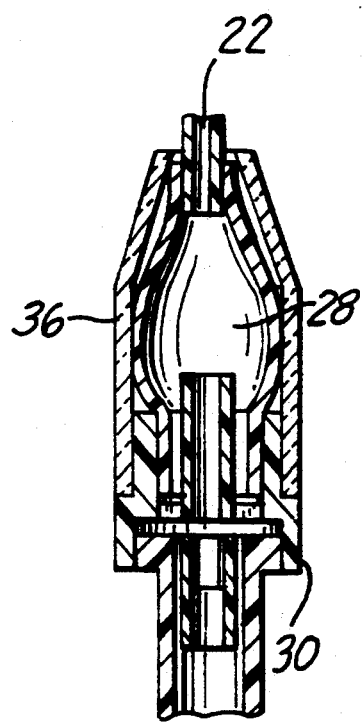
FIG. 3 is a sectional view of the reservoir of the FIG. 1 needle system showing the tube entering therein.

Referring now to the drawings the reference numeral 10 generally denotes the needle system of the present invention. Needle assembly 10 includes an elongated needle 12 having a distal end 14 and a proximal end 16. Distal end 14 is shaped and dimensioned for introduction into the vascular system. Elongated needle 12 has a predetermined volume. A needle hub 18 is situated at the proximal end 16 of the needle 12. The needle hub 18 has a predetermined volume. A port 20 is positioned between the proximal end of the needle hub and the proximal needle end.

A visualization connector tube 22 is provided. Connector tube 22 has a first end 24 and a second end 26. First end 24 of tube 22 is in communication with port 20. Tube 22 has a predetermined volume. Tube 22 is sufficiently clear to permit visualization of material therein and, in the preferred embodiment of the invention the tube is formed of a clear polyvinyl chloride.

An elastomeric reservoir 28 is provided. Reservoir 28 in free, direct, unrestricted two-way communication with the second end 26 of the tube 22. Elastomeric reservoir 28 has an initial unexpanded state in which it has a first pressure and a first volume. Elastomeric reservoir 28 has a second expanded state in which it has a second pressure and a second volume.

In the preferred embodiment of the invention reservoir 28 is tapered in shape. When injections are made through reservoir 28 the taper minimizes turbulence.

In the preferred embodiment of the invention, the first pressure of the reservoir is approximately equal to ambient air pressure, and the second pressure of the reservoir correlates to human blood pressure.

Needle system 10 includes a gasket 27 which in the preferred embodiment is a slit, silicone diaphragm disk. A guidewire (not shown) can be passed into the gasket and into needle 12. The guidewire is passed through an opening 18a in the hub. When the guidewire passes through the gasket, the gasket provides a barrier to the flow of blood. Thus, blood which enters the needle, under pressure, cannot exit from the hub.

To allow the needle system to provide a selectively closed system, proximal to the reservoir, a syringe valve 30 or stopcock, or other appropriate mechanism is provided.

In a preferred embodiment of the invention, tube 22 has markings 34 which indicate approximate blood pressure. The first marking 34a on tube 22 is about 0.20 inches from the point the tube 22 connects to the hub 18. Subsequent markings are spaced from one another by 0.39 inches. The first marking 34a corresponds to a pressure of about 40 mm Hg and the distance between each marking corresponds to about 20 mm Hg.

Needle 12 has an internal diameter of between 0.018 and 0.075 inches, a length of between 0.5 and 6.0 inches, and a volume of between 0.000127 and 0.026507 cubic inches. The needle hub 18 is formed with a volume of between 0.0005 and 0.003 cubic inches. Tube 22 is formed with an internal diameter of between 0.020 and 0.100 inches, a length of between 2.0 and 8.0 inches and a volume of between 0.0006 and 0.063 cubic inches. Reservoir 28 is formed with a volume of between 0.010 and 0.060 cubic inches. In the preferred embodiment of the invention the needle 12 has an internal diameter of about 0.042 inches, a length of about 3.0 inches and a volume of about 0.0042 cubic inches. In the preferred embodiment the hub has a volume of about 0.001 cubic inches. In the preferred embodiment of the invention tube 22 has an internal diameter of about 0.070 inches, a length of about 5.0 inches and a volume of about 0.019 inches. In this preferred embodiment, the reservoir in its first state has a volume of about 0.025 cubic inches (at ambient pressure) and its second state a volume of about 0.040 cubic inches at a pressure of 300 mmHg (5.77 psi).

In use, needle system 10 works as follows. When elongated needle 12 is placed in an artery, the arterial blood which is under pressure, displaces and compresses the air that is contained in needle 12, hub 18, and a portion of the tube 22. The displaced, compressed air migrates into reservoir 28 causing reservoir 28 to expand to its expanded state. As the air pressure in the elastomeric reservoir 28 equals the blood pressure, continuous visualization of pulsatile blood flow can be seen in tube 22. The actual distance that blood travels up tube 22 can be varied by varying the internal dimensions or material compositions of the various components of the system and thereby the volume of available compressible air.

When needle 12 is placed in an artery, syringe activated valve 30 is positioned to insure that the system is closed. In lieu of a syringe activated valve a stopcock can be used.

The relationship between pressure and volume of air in this closed system can be closely approximated by the following expression for isentropic compression of air.

$$V_2/V_1 = (P_1/P_2)^{0.71} \tag{1.1}$$

The relationship between the first and second volumes and first and second pressures of the air contained in the closed needle system of the preferred embodiment can be defined by equation (1.1) where:

V1 = the volume of the needle system which includes the needle, hub, visualization connector tube and the initial unexpanded volume of the elastomeric reservoir, V2 = the original volume of the unexpanded elastomeric reservoir plus the volume of the expanded portion of the elastomeric reservoir plus a chosen percentage of the connector tube left unfilled with blood, P1 = the ambient air pressure (i.e. 14.7 psi at standard conditions), P2 = the ambient air pressure plus internal blood pressure, The closed system initial volume, V1, can be expressed as;

$$V1 = Vn + Vh + Vt + Vr \tag{1.2}$$

Where:

Vn = the volume of the needle,
Vh = the volume of the needle hub,
Vt = the volume of the visualization connector tube,
Vr = the initial unexpanded volume of the elastomeric reservoir.

The second volume of air, V2, is equal to the original unexpanded reservoir volume (Vr) plus the expanded volume of the elastomeric reservoir at P2 ($\Delta$Vr) plus a chosen percentage (L) of the pulsatile visualization connector tube left unfilled with blood.

$$V2 = Vr + \Delta Vr + L(Vt) \tag{1.3}$$

In the preferred embodiment, the change in the volume of the elastomeric reservoir $\Delta$Vr is a function of the pressure P2, as P2 increases, the volumetric expansion $\Delta$Vr increases.

Solving equation (1.1) for V2, $$V_2 = (P_1/P_2)^{0.71}(V1) \tag{1.4}$$

and substituting for V2 from equation (1.3), $$Vr + \Delta Vr + L(Vt) = (P_1/P_2)^{0.71}(V1) \tag{1.5}$$

In order for pulsatile visualization of arterial blood to occur, the air contained in the needle, needle hub and a portion of the visualization connector tube must be displaced or compressed into the remaining portions of the closed needle system.

The desired percentage (L) of the visualization connector tube remaining filled with air or unfilled with blood at P2 can be determined by, $$L = ((P_1/P_2)^{0.71}(V1) - (Vr + \Delta Vr))/Vt \tag{1.6}$$

The percentage of the connector tube filled with blood (Lf) at any given set of conditions can be determined by, $$Lf = 1 - ((P1/P2)^{0.71}(V1) - (Vr + \Delta Vr))/Vt \qquad (1.7)$$

As the needle 12 enters the artery, P2 is determined by the arterial blood pressure which continually pulsates from the systolic to the diastolic blood pressure. Likewise, as P2 pulsates, the percentage of the connector tube filled with blood pulsates according to equation (1.7). This effect allows the user to visually verify needle placement using the closed needle system. The shape, length and volume of the visualization connector tube are dimensioned to allow visualization of the arterial pulse over the full range of blood pressures.

In system 10, due to the provision of elastomeric reservoir 28, when pressure increases, air is displaced from the needle, hub, and tube by two mechanisms: compression and reservoir expansion. In contrast, a rigid system having no elastomeric element can only allow air displacement by a single mechanism: compression. The provision of two mechanisms for air displacement facilitates air displacement and results in a greater percentage of tube 22 being available for visualization then would be available in a rigid system. To achieve the same area for visualization in a rigid system as is provided in system 10 would require that the volume of the entire system be increased. This would result in a more cumbersome system. Although system 10 uses an elastomeric reservoir, similar advantages could be achieved by making another element of the system, such as the hub or tube, elastomeric.

As shown in the drawings elastomeric reservoir 28 may be housed in a rigid protective enclosure 36 to prevent accidental squeezing or manipulation of the elastomeric reservoir 28. Rigid housing 36 further controls and limits the expansion of the flexible reservoir 28 to allow test injections and road mapping for needle placement verification.

In the preferred embodiment of the invention reservoir 28 is made of polyvinyl chloride, hub 18 is made of polycarbonate and the needle 12 is made of stainless steel.

What is claimed:

1. A needle system usable for vascular access, said system comprising:
    an elongated needle having a distal end and a proximal end, the distal end shaped and dimensioned for introduction into a vascular system, said elongated needle having a predetermined volume;
    a needle hub at the proximal end of said needle, said needle hub having a predetermined volume;
    a port positioned between said proximal needle end and proximal hub end;
    a visualization connector tube having a first end and a second end, said first end being in communication with said port, said tube having a predetermined volume and being sufficiently clear to permit visualization of material therein;
    an elastomeric reservoir in free, direct, unrestricted two-way communication with said second end of said tube, said reservoir having an initial unexpanded state and a second expanded state; and
    a rigid housing enclosing said elastomeric reservoir; pressure in said needle system increasing when said elongated needle is introduced into the vascular system, said pressure increase causing the air in said needle system to compress and migrate, said reservoir expanding to said expanded state in response to said compression and migration of air in said needle system, said compression of air causing the volume of air in said needle system to decrease while said volume of air in said reservoir increases.

2. The needle system of claim 1 wherein said first pressure is approximately equal to ambient air pressure and wherein said second pressure correlates to human blood pressure plus ambient air pressure.

3. The needle system of claim 1 and further comprising a gasket means for sealing said proximal needle end, said gasket means formed such that a guidewire may be passed therethrough, said gasket means preventing blood flow outwardly from said proximal needle end.

4. The reservoir system in claim 1 and including a syringe activated valve.

5. The needle system of claim 1 wherein said reservoir is formed of polyvinylchloride.

6. The needle system of claim 1 wherein said visualization connector tube is formed of a clear polyvinylchloride.

7. The needle system of claim 1 and further comprising marking means on said tube, said marking means providing an approximate indication of blood pressure.

8. The needle system of claim 1 wherein arterial pulsatile visualization is visible in the visualization connector tube for blood pressures of 60 to 300 mmHg.

9. The needle system of claim 1 wherein said elongated needle has a volume of between 0.000127 and 0.026507 cubic inches, said tube has a volume of between 0.0006 and 0.063 cubic inches, said reservoir has a volume of between 0.010 and 0.060 cubic inches and said internal hub has a volume of between 0.0005 and 0.003 cubic inches.

10. The needle system of claim 9 wherein said needle has an internal diameter of between 0.018 and 0.075 inches and a length of between 0.5 and 6.0 inches and said visualization connector tube has a length of between 2.0 and 8.0 inches and an internal diameter of between 0.020 and 0.100 inches.

11. The needle system of claim 10 wherein said needle has a length of about 3 inches, an internal diameter of about 0.042 inches and a volume of about 0.0042 cubic inches, said hub has a volume of about 0.001 cubic inches, said tube has an internal diameter of about 0.070 inches and a length of about 5.0 inches and a volume of about 0.019 cubic inches and said reservoir has a first volume of about 0.025 cubic inches and a second volume of about 0.040 cubic inches at a pressure of 300 mmHg (5.77 psi).

12. The needle system of claim 7 wherein the first marking is about 0.20 inches from the needle hub and subsequent markings are spaced apart by about 0.39 inches.

13. The needle system of claim 11 and further comprising marking means on said tube; said marking means providing an approximate indication of blood pressure and wherein said first marking of said marking means correlates to a pressure of about 40 mm Hg and each subsequent marking corresponds to an incremental increase of about 20 mm Hg.

* * * * *